(12) United States Patent
Kim

(10) Patent No.: US 6,461,369 B1
(45) Date of Patent: Oct. 8, 2002

(54) HAIR TRANSPLANTER

(76) Inventor: Jung Chul Kim, #103-102 Changsin Apt., 1336 Beommool-dong, Soosung-ku, Taegu-shi 706-100 (KR)

( * ) Notice: Subject to any disclaimer, the term of this patent is extended or adjusted under 35 U.S.C. 154(b) by 0 days.

(21) Appl. No.: 09/806,896

(22) PCT Filed: May 29, 2000

(86) PCT No.: PCT/KR00/00550

§ 371 (c)(1), (2), (4) Date: Jun. 11, 2001

(87) PCT Pub. No.: WO01/10307

PCT Pub. Date: May 15, 2000

(30) Foreign Application Priority Data

Aug. 5, 1999 (KR) .............................. 99-32165

(51) Int. Cl.⁷ .............................................. A61B 17/34
(52) U.S. Cl. ........................................................ 606/187
(58) Field of Search .......................... 606/1, 133, 187; 604/164, 264; 623/15

(56) References Cited

U.S. PATENT DOCUMENTS

| 4,160,453 A | * | 7/1979 | Miller | 606/187 |
|---|---|---|---|---|
| 5,036,860 A | * | 8/1991 | Leigh et al. | 600/567 |
| 5,417,683 A | * | 5/1995 | Shiao | 606/1 |
| 5,439,475 A | * | 8/1995 | Bennett | 606/187 |
| 5,562,613 A | * | 10/1996 | Kaldany | |
| 5,782,851 A | * | 7/1998 | Rassman | 606/187 |
| 5,817,120 A | * | 10/1998 | Rassman | 606/187 |
| 5,951,572 A | * | 9/1999 | Markman | 606/133 |
| 6,059,807 A | * | 5/2000 | Boudjema | 606/187 |

FOREIGN PATENT DOCUMENTS

| JP | 4-152944 | 5/1992 |
|---|---|---|
| JP | 6-315493 | 11/1994 |
| JP | 10-052429 | 2/1998 |

* cited by examiner

Primary Examiner—Michael J. Milano
Assistant Examiner—Vy Q. Bui
(74) Attorney, Agent, or Firm—Greer, Burns & Crain, Ltd.

(57) ABSTRACT

The present invention discloses a hair trasplanter. A needle to be inserted into a scalp has a pointed end portion to reduce damage of the scalp, and a guide plate in adhered to an end portion of a sliding unit reciprocating in the longitudinal direction of the needle outside the needle, in order to prevent hair roots from being separated at the time of the separation of the needle. As a result, the hair roots inserted into a needle insertion groove are not damaged and are naturally settled in the scalp without modification, thereby stably performing the hair transplantation.

7 Claims, 4 Drawing Sheets

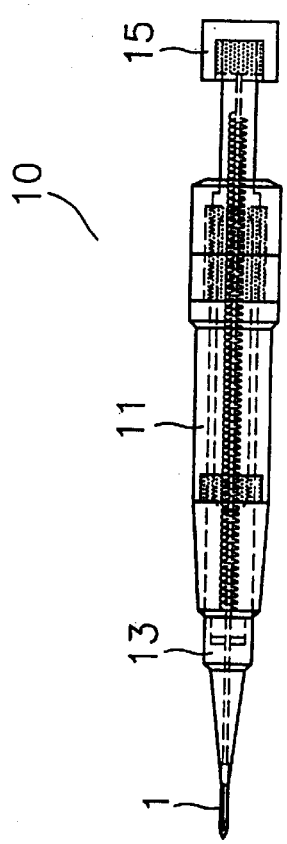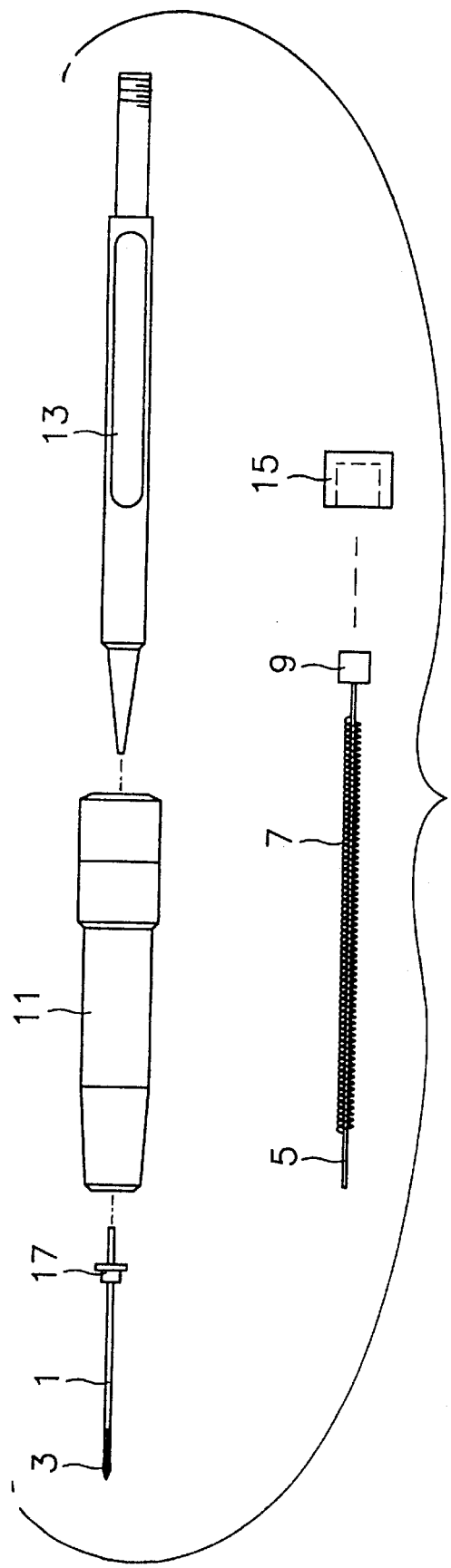
Fig.1A (PRIOR ART)
Fig.1B (PRIOR ART)

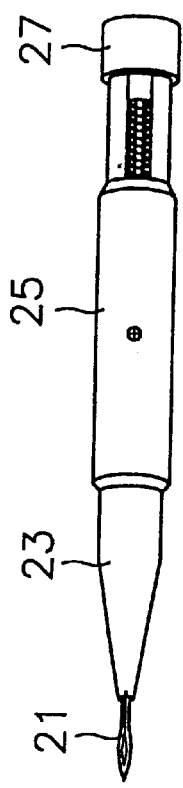
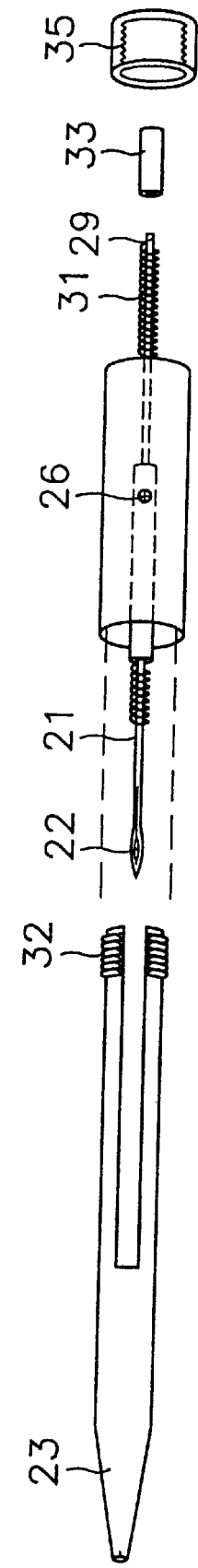
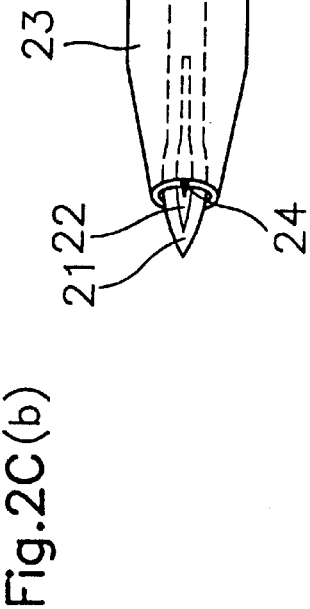
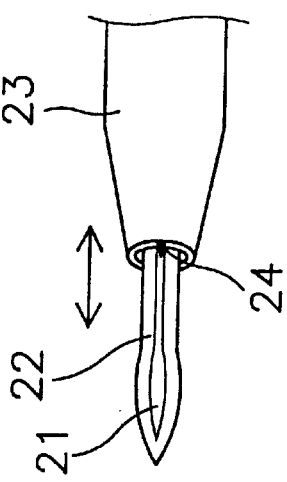
Fig.2A
Fig.2B
Fig.2C(a)
Fig.2C(b)

HAIR TRANSPLANTER

BACKGROUND OF THE INVENTION

1. Field of the Invention

The present invention relates to a hair transplanter, and in particular to an improved hair transplanter which can stably settle hair roots inserted with a needle in a predetermined position of a scalp in a hair transplantation operation, without causing deformation or damage to the hair roots.

2. Description of the Background Art

FIGS. 1a and 1b illustrate a conventional hair transplanter. FIG. 1a is a schematic view of an assembled hair transplanter, and FIG. 1b is a decomposition view of the hair transplanter in FIG. 1a. FIG. 1c shows an operation state of the hair transplanter for smoothly transplanting hair roots.

As shown therein, the conventional hair transplanter 10 includes: a needle 1 having its end portion inserted with hair roots into a predetermined position of a scalp; a handle unit 11 in which the needle 1 is disposed; a sliding member 13 inserted into the handle unit 11, for moving in a longitudinal direction of the handle unit 11 by a predetermined distance; and a guide bar 5 passing through the inside of the sliding member 13 in its longitudinal direction.

When a compression unit 15 positioned at a rear end portion of the hair transplanter 10 is pushed to a front portion, the guide bar 5 moves along the inside of the needle 1. Referring to FIG. 1c, when passing the end portion of the needle 1 where the hair roots are inserted, the guide bar 5 separates the hair roots from the needle 1. That is, the guide bar 5 moving along an inside through hole of the needle 1 pushes the hair roots in the needle 1, and settles them in the scalp. However, the hair roots to be transplanted are inserted into the scalp, and thus deformed or damaged due to a physical force. Accordingly, the hair roots are settled in the scalp after an extended period of time, and a settlement rate thereof is decreased.

In addition, in the conventional hair transplanter 10, the end portion of the needle 1 is formed at a predetermined angle, and thus is not smoothly inserted into the scalp, thereby often damaging the scalp to bleed.

SUMMARY OF THE INVENTION

Accordingly, it is an object of the present invention to provide a hair transplanter which can minimize damage of a scalp due to insertion of a needle by forming the needle to have a pointed end portion, and which can stably perform the hair transplantation by preventing damage of hair roots inserted into the needle.

In order to achieve the above-described object of the present invention, there is provided a hair transplanter for transplanting hairs with hair roots into a scalp, including: a needle having a groove of a predetermined length at its end portion so that hair roots can be inserted; a handle unit disposing the needle at its front center portion, and having an empty space of a predetermined size at its inside portion, and a compression support unit combined or separated in its longitudinal direction at its rear portion; a sliding member inserted into the handle unit, for reciprocating in a longitudinal direction by a predetermined distance due to an external force, the needle in the handle unit passing through the inside center portion of the sliding member so that the end portion of the needle can be protruded by a predetermined length; a spring member connected to the compression support unit, for restoring the sliding member moving to the front portion due to the external force to a rear portion; and a compression unit provided at the end portion of the compression support unit, for moving the sliding member to the front portion due to the external force.

In addition, there is provided a hair transplanter for transplanting hairs with hair roots into a scalp, including: a sliding member having a plurality of through holes in its longitudinal direction at predetermined intervals, a plurality of needles passing through the through holes, guide plates protruded from the respective through holes for preventing hair roots from being separated from the upper portions of needle grooves being disposed on the front surface of the sliding member, a connection support unit being adhered to the rear surface of the sliding member; the plurality of needles inserted into the through holes of the sliding member, the hair roots being inserted into their grooves; a handle unit having at its inside portion a through hole which the connection support unit passes through, the plurality of needles being provided on the front surface of the handle unit; a spring member connected to the connection support unit protruding from the handle unit; and a compression unit internally having the spring member, moving into the handle unit by a predetermined distance, and moving the sliding member.

BRIEF DESCRIPTION OF THE DRAWINGS

The present invention will become better understood with reference to the accompanying drawings which are given only by way of illustration and thus are not limitative of the present invention, wherein:

FIG. 1a is a perspective view illustrating a conventional hair transplanter;

FIG. 1b is a decomposition view illustrating the hair transplanter in FIG. 1a;

FIG. 2a is a perspective view illustrating a hair transplanter in accordance with a first embodiment of the present invention;

FIG. 2b is a perspective view illustrating the decomposition state of the hair transplanter in FIG. 2a;

FIG. 2c shows an operation state of the hair transplanter in FIG. 2a;

FIG. 3b is a decomposition view illustrating the hair transplanter in FIG. 3a; and FIG. 3c shows a shape of a guide plate of the hair transplanter in FIG. 3a.

DETAILED DESCRIPTION OF THE PREFERRED EMBODIMENTS

Figure 1C:
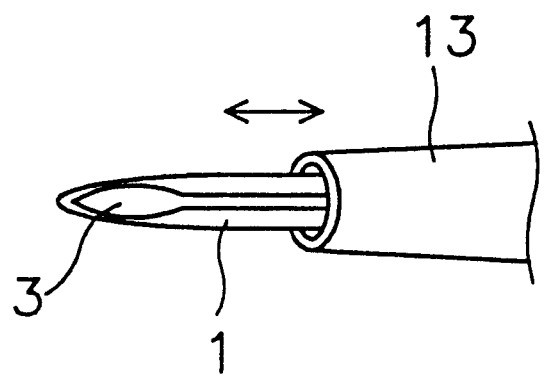
FIG. 1c shows an operation state of the conventional hair transplanter.
Figure 1C:
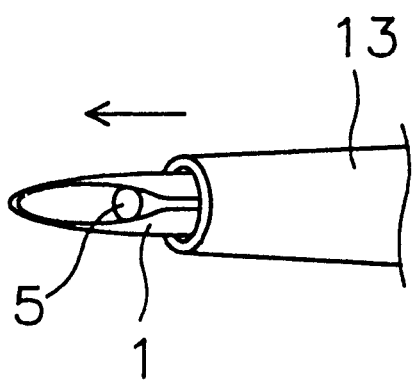
Figure 1C:
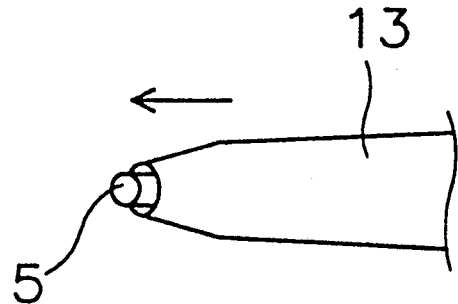

A hair transplanter in accordance with preferred embodiments of the present invention will now be described in detail with reference to the accompanying drawings.

FIG. 2a is a perspective view illustrating the hair transplanter in accordance with a first embodiment of the present invention, FIG. 2b is a perspective view illustrating the decomposition state of the hair transplanter in FIG. 2a, and FIG. 2c shows an operation state of the hair transplanter in FIG. 2a. As illustrated therein, the hair transplanter 30 includes: a needle 21 configured and adapted to receive hair roots at its end portion; a handle unit 25 disposing the needle 21 at its front center portion, and having an empty space of a predetermined size at its inside portion; a sliding member 23 inserted into the handle unit 25, for reciprocating in its longitudinal direction by a predetermined distance due to an external force, the needle 21 in the handle unit 25 passing through the inside center portion of the sliding member 23 so that the end portion of the needle 21 can be protruded by a predetermined length; a compression support unit 29 protruding from the rear portion of the handle unit 25 in its longitudinal direction by predetermined length; a spring member 31 connected to a compression support unit 29; and a compression unit 35 provided at the end portion of the compression support unit 29, for connecting to the protruded end portion of the sliding member 23 passing through the inside of the handle unit 25.

Therefore, when the rear end compression unit 35 of the hair transplanter 30 is compressed, the sliding member 23 moves to a front portion in a longitudinal direction by a predetermined length. When a compression force is removed, the sliding member 23 is moved to an original position due to a force of the spring member 31.

Referring to FIG. 2c, when moving to the front portion, the sliding member 23 is positioned at the end portion of the needle 21. Accordingly, when the needle 21 is inserted into the scalp and then separated from the scalp, a guide plate 24 at the end portion of the sliding member 23 prevents deformation and damage of the hair roots.

That is, in the initial combination state of the hair transplanter 30 as depicted in FIG. 2c(a), the end portion of the needle 21 is protruded from the end portion of the sliding member 23 by a predetermined length. Here, the hair roots (not shown) are inserted into the insertion groove 22 of the needle 21. In this case, the needle 21 is inserted into a predetermined position on the scalp. As the compression unit 35 gets compressed, the sliding member 23 moves to the predetermined position in a generally vertical direction. As a result, the needle 21 gets separated from the scalp leaving the hair roots in their place.

At this time, in order to prevent the hair roots from being separated when the needle 21 is separated, the guide plate 24 having an identical size to a width of the needle insertion groove 22 is provided at the front surface of the needle insertion groove 22 in the both side end portions of the sliding member 23, thereby preventing deformation, damage and separation of the hair roots.

As a result, in the hair transplanter 30 in accordance with the first embodiment of the present invention, when the needle 21 is separated from the scalp at the outside of the needle insertion groove 22, the guide plate 24 disposed at the end portion of the sliding member 23 prevents the hair roots from being separated from the scalp, thereby overcoming deformation and damage of the hair roots due to a direct contact between the hair roots and the guide bar in the conventional hair transplanter.

Figure 3A:
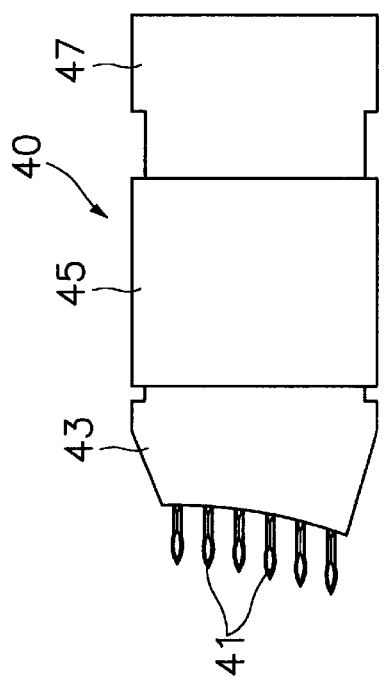
FIG. 3a is a schematic view illustrating a hair transplanter in accordance with a second embodiment of the present invention.
Figure 3B:
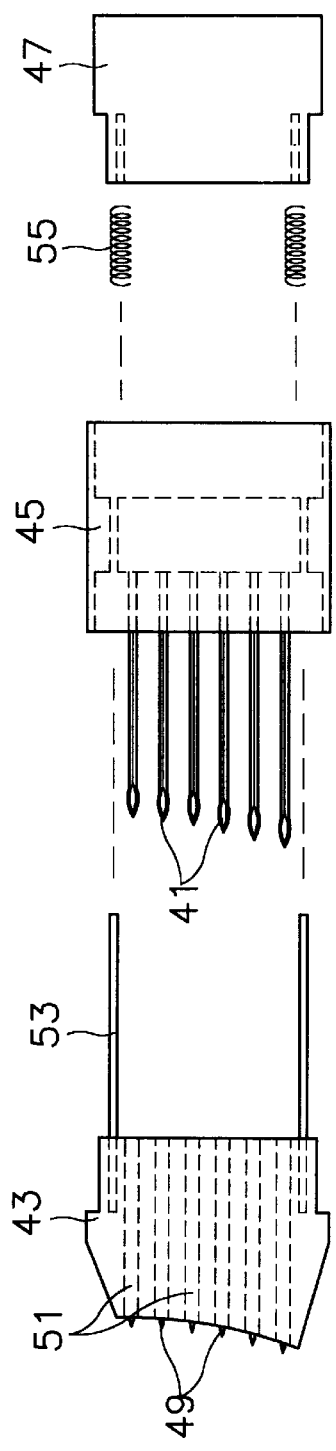

On the other hand, FIGS. 3a and 3b illustrate the hair transplanter in accordance with a second embodiment of the present invention. FIG. 3a is a schematic view illustrating the hair transplanter, and FIG. 3b is a decomposition view illustrating the hair transplanter in FIG. 3a.

As illustrated therein, the hair transplanter 40 of the second embodiment is formed in an identical principle to the hair transplanter of the first embodiment, except for providing a plurality of needles and guide plates. As a result, a plurality of hairs can be transplanted at a time.

That is, the hair transplanter 40 has the plurality of needles 41, for example 2 to 10 needles (6 needles in this embodiment). Second guide plates 49 are respectively disposed at the front surfaces of needle insertion grooves of the end portions of the needles 41. A sliding member 43 is moved to a front/rear portion by compressing a compression unit 47 positioned at the rear portion. Thus, the second guide plates 49 pass the front surfaces of the needle insertion grooves, thereby preventing the hair roots from being separated from the scalp when the needles are separated.

Figure 3C:
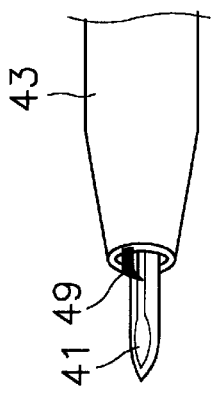

On the other hand, referring to FIG. 3c, the end portion of the guide plate 49 is curved in a downward direction, and thus easily prevents the hair roots from being separated from the scalp.

In addition, differently from the conventional hair transplanter, the needles 21, 41 of the hair transplanters 30, 40 have a double-bent shape, so that their end portions are more pointed. Accordingly, the needles 21, 41 can be more easily inserted into the scalp, and thus minimize bleeding.

The handle unit 25 of the hair transplanter 30 can be re-used by means of sterilization. Besides, the needle is connected to the handle unit 25 by a screw 26, and thus it is possible to replace the needle by loosening the screw 26.

As discussed earlier, in accordance with the present invention, the needle is formed to have a pointed end portion to reduce damage of the scalp due to the insertion and separation of the needle into and from the scalp. In addition, the guide plate is provided at the end portion of the sliding member moving in the longitudinal direction of the needle outside the needle. Accordingly, when the needle is separated from the scalp, the guide plate at the front surface of the needle contacts the hair roots with a minimum pressure, thereby minimizing damage of the scalp, stably settling the hair roots in the scalp, and maximizing a settlement rate of the hair roots.

Moreover, the needle can be provided in a main body of the hair transplanter, thereby improving efficiency. Also, the hair transplanter can be semipermanently employed by replacing the needle.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

What is clammed is:

1. A hair transplanter for transplanting hair with hair roots into a scalp, comprising:

a needle for making an incision in the scalp, and having a groove of a predetermined length at an end portion for receiving at least one hair root;

a handle unit disposing the needle at a front center portion, and having an empty space of a predetermined size at an inside portion, and a compression support unit combined or separated in a longitudinal direction at a rear portion;

a sliding member inserted into the handle unit, and having a guide plate at a front end, the sliding member reciprocating in a longitudinal direction by a predetermined distance when an external force is applied to the sliding member, the needle in the handle unit passing through an inside center portion of the sliding member so that the end portion of the needle protrudes from the sliding member by a predetermined length, and the guide plate slidingly engaging the groove of the needle to prevent the hair root from being separated from the scalp;

a spring member connected to the compression support unit for restoring the sliding member to a rear portion of the handle unit when the sliding member has been moved to the front center portion by the external force; and a compression unit provided at an end portion of the compression support unit for moving the sliding member to the front center portion when the external force is applied to the compression unit.

2. The hair transplanter according to claim 1, wherein the guide plate is approximately the size of a width of the groove of the needle.

3. The hair transplanter according to claim 1, wherein the end portion of the needle is double-bent to be easily inserted into the scalp.

4. The hair transplanter according to claim 1, wherein the needle is removably connected to the handle unit by a screw.

5. A hair transplanter for transplanting hair with hair roots into a scalp, comprising:

a sliding member having a plurality of through holes in a longitudinal direction at predetermined intervals, a guide plate protruding from a front end of the sliding member into each of the through holes, a connection support unit being adhered to a rear surface of the sliding member;

a plurality of needles for making incisions in the scalp inserted into the through holes of the sliding member, each of the needles having a groove for receiving at least one hair root, each of the guide plates slidingly engaging a corresponding one of the grooves to prevent the hair roots from being separated from the scalp;

a handle unit having at an inside portion a through hole which the connection support unit passes through, the plurality of needles being provided on the front surface of the handle unit;

a spring member connected to the connection support unit protruding from the handle unit; and a compression unit for internally receiving the spring member, and adapted to be pushed into the handle unit by a predetermined distance for moving the sliding member.

6. The hair transplanter according to claim 5, wherein the number of the needles is at least 2.

7. The hair transplanter according to claim 5, wherein each of the needles has a double-bent end portion in order to be easily inserted into the scalp.

* * * * *